United States Patent
Shi et al.

(10) Patent No.: US 9,586,895 B2
(45) Date of Patent: Mar. 7, 2017

(54) DIMETHYLSULFOXIDE PREPARATION METHOD

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Chunfeng Shi, Beijing (CN); Min Lin, Beijing (CN); Xingtian Shu, Beijing (CN); Xuhong Mu, Beijing (CN); Bin Zhu, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

(*) Notice: Subject to any disclaimer, the term of this patent is extended or adjusted under 35 U.S.C. 154(b) by 0 days.

(21) Appl. No.: 14/439,562

(22) PCT Filed: Oct. 29, 2013

(86) PCT No.: PCT/CN2013/001305
§ 371 (c)(1),
(2) Date: Apr. 29, 2015

(87) PCT Pub. No.: WO2014/067235
PCT Pub. Date: May 8, 2014

(65) Prior Publication Data
US 2015/0284322 A1    Oct. 8, 2015

(30) Foreign Application Priority Data
Oct. 29, 2012 (CN) .......................... 2012 1 0419836

(51) Int. Cl.
*C07C 315/02* (2006.01)
*C07C 319/14* (2006.01)
*C07C 317/04* (2006.01)

(52) U.S. Cl.
CPC .......... *C07C 315/02* (2013.01); *C07C 319/14* (2013.01); *Y02P 20/127* (2015.11)

(58) Field of Classification Search
CPC .... C07C 319/14; C07C 315/02; C07C 317/04
USPC .......................................... 568/27
See application file for complete search history.

(56) References Cited

U.S. PATENT DOCUMENTS 2,910,506 A    10/1959  Folkins et al.
2007/0095646 A1*  5/2007  Wu .................... B01D 3/009
                                                            203/29

FOREIGN PATENT DOCUMENTS

| CN | 1217326 A | 5/1999 |
| CN | 1301599 A | 7/2001 |
| CN | 1132699 C | 12/2003 |
| CN | 102838516 A | 12/2012 |
| CN | 103288691 A | 9/2013 |

OTHER PUBLICATIONS

Reddy et al., An improved process for the production of alkyl sulfoxide and/or arylsulfoxide and sulfone, IN 183627 abstract, Mar. 2000.*
Upadhya et al., An improved process for the preparation of sulfoxides, IN 185701 abstract, Apr. 2001.*
Vasile Hulea et al., "Thioether oxidation by hydrogen peroxide using titanium-containing zeolites as catalysts", Journal of Molecular Catalysis A: Chemical, vol. 111, Issue 3, Sep. 25, 1996, pp. 325-332.
Katarzyna Kaczorowska et al., "Oxidation of sulfides to sulfoxides. Part 2: Oxidation by hydrogen peroxide", Tetrahedron, vol. 61, Issue 35, Aug. 29, 2005, pp. 8315-8327.
"Dimethyl sulfide", Wikipedia, the free encyclopedia, Jun. 23, 2015, URL: https://en.wikipedia.org/wiki/Dimethl_sulfide.
Jialin Tao et al., "Cyclohexane Oxidation Catalyzed by Titanuim Silicalite (TS-1) With Hydrogen Peroxide", Journal of Natural Gas Chemistry, vol. 10, No. 4, 2001, pp. 295-307.
Ravinder S. Reddy et al.; "Sulfoxidation of Thioethers using Titanium Silicate Molecular Sieve Catalysts" Journal of the Chemical Society, Chemical Communications. 1992, No. 2, pp. 84-85.
Qian, Ling et al. "Study on the Technology of Preparing Dimethyl Sulfoxide" Chemical World, ISSN 0367-6358, 2003, No. 1, pp. 36, 37, 48.
S. K. Bharadwaj et al. "Chemoselective sulfoxidation by H2O2 or HNO3 using a phosphate impregnated titania catalyst" Tetrahedron Letters, 2009, 50(27), pp. 3767-3771.

* cited by examiner

*Primary Examiner* — Jafar Parsa
(74) *Attorney, Agent, or Firm* — Novick, Kim & Lee, PLLC; Allen Xue

(57) ABSTRACT

A process for producing dimethyl sulfoxide, wherein said process comprises the following steps: (1) contacting hydrogen sulfide with methanol to produce a mixture containing dimethyl sulfide, and separating dimethyl sulfide from the mixture; and (2) in the presence or absence of a solvent, contacting dimethyl sulfide obtained in step (1) with at least one oxidant and a catalyst to produce a mixture containing dimethyl sulfoxide, said catalyst comprises at least one Ti—Si molecular sieve.

24 Claims, 1 Drawing Sheet

DIMETHYLSULFOXIDE PREPARATION METHOD

TECHNICAL FIELD

The present invention relates to a process for producing dimethyl sulfoxide.

BACKGROUND ART

Currently, dimethyl sulfoxide is generally produced by the oxidation of dimethyl sulfide. The common production methods are as follows.
1. Methanol-Carbon Disulphide Method: methanol and carbon disulphide are used as starting material with γ-Al$_2$O$_3$ as the catalyst to firstly synthesize dimethyl sulfide. Then the resulting dimethyl sulfide is oxidized with nitrogen dioxide (or nitric acid) to produce dimethyl sulfoxide.
2. Nitrogen Dioxide Method: methanol and hydrogen sulfide are used as starting material in the presence of γ-alumina to produce dimethyl sulfide; sulfuric acid and sodium nitrite are reacted to produce nitrogen dioxide; the resulting dimethyl sulfide and nitrogen dioxide are subjected to oxidation at 60-80° C. to produce a crude dimethyl sulfoxide, or the resulting dimethyl sulfide is directly oxidized with oxygen gas to produce a crude dimethyl sulfoxide; and the crude dimethyl sulfoxide is subjected to a vacuum distillation to produce a refined dimethyl sulfoxide.
3. Dimethyl Sulfate Method: dimethyl sulfate and sodium sulphide are reacted to produce dimethyl sulfide; sulfuric acid and sodium nitrite are reacted to produce nitrogen dioxide; dimethyl sulfide and nitrogen dioxide are subjected to oxidation to produce a crude dimethyl sulfoxide, which is neutralized and distilled to produce a refined dimethyl sulfoxide.

In addition, dimethyl sulfoxide can also be produced from dimethyl sulfide by the anode oxidation method.

CONTENTS OF INVENTION

The object of the present invention is to provide a continuous process for producing dimethyl sulfoxide, which process can not only provide a higher selectivity for dimethyl sulfoxide, but also provides a higher dimethyl sulfide conversion and a higher oxidant utility.

It is found by the present inventors that dimethyl sulfide, obtained by the reaction of hydrogen sulfide and methanol, after separation, can be contacted with an oxidant in the presence of a Ti—Si molecular sieve to produce dimethyl sulfoxide, the reaction conditions are mild, and a high dimethyl sulfide conversion, a high oxidant utility and a high selectivity for dimethyl sulfoxide can be obtained. Based on the above, the present invention is completed.

The present invention provides a process for producing dimethyl sulfoxide, which comprises the following steps:
(1) contacting hydrogen sulfide with methanol to produce a mixture containing dimethyl sulfide, and separating dimethyl sulfide from the mixture; and
(2) in the presence or absence of a solvent, contacting dimethyl sulfide obtained in step (1) with at least one oxidant and a catalyst to produce a mixture containing dimethyl sulfoxide, said catalyst comprises at least one Ti—Si molecular sieve.

Specifically, the present invention has the following technical schemes:
1. A process for producing dimethyl sulfoxide, wherein said process comprises the following steps:
(1) contacting hydrogen sulfide with methanol to produce a mixture containing dimethyl sulfide, and separating dimethyl sulfide from the mixture; and
(2) in the presence or absence of a solvent, contacting dimethyl sulfide obtained in step (1) with at least one oxidant and a catalyst to produce a mixture containing dimethyl sulfoxide, said catalyst comprises at least one Ti—Si molecular sieve.
2. The process according to any of previous schemes, wherein the contact in step (2) is conducted in the reaction zone of a catalytic distillation reactor, a mixture containing an unreacted dimethyl sulfide is obtained at the top of the catalytic distillation reactor, the mixture containing dimethyl sulfoxide is obtained at the bottom of the catalytic distillation reactor, the reaction zone is loaded with the catalyst.
3. The process according to any of previous schemes, wherein the oxidant is fed from the first feeding port to the reaction zone, or the oxidant and the solvent are fed from the first feeding port to the reaction zone;
dimethyl sulfide is fed from the second feeding port to the reaction zone;
the theoretical column plate number from the first feeding port to the bottom of the reaction zone is T1, the theoretical column plate number from the second feeding port to the bottom of the reaction zone is T2, T1>T2.
4. The process according to any of previous schemes, wherein the theoretical column plate number of the reaction zone is T, the ratio of T1 to T as percent is 50-100%, the ratio of T2 to T as percent is 10-80%.
5. The process according to any of previous schemes, wherein the ratio of T1 to T as percent is 80-100%, the ratio of T2 to T as percent is 10-30%.
6. The process according to any of previous schemes, wherein
based on the total weight of the streams in the reactor, the content of the catalyst is 1-50 wt %; or the mass ratio of dimethyl sulfide and the catalyst is 0.1-100:1; or
the contact is performed in a fixed bed reactor, the weight hourly space velocity of dimethyl sulfide was 0.1-10000 h$^{-1}$.
7. The process according to any of previous schemes, wherein said catalyst comprises the Ti—Si molecular sieve and the support, based on the total amount of the catalyst, the content of the Ti—Si molecular sieve is 10-99 wt %, the content of the support is 1-90 wt %.
8. The process according to any of previous schemes, wherein the preparation of the catalyst comprises: under a hydrolysis reaction condition, at least one organosilicon compound capable of hydrolysis and at least one water-soluble alkali are contacted with water, the mixture obtained by the contacting is mixed with the Ti—Si molecular sieve, the resulting mixture is granulated and calcined.
9. The process according to any of previous schemes, wherein the Ti—Si molecular sieve, the organosilicon compound, the water-soluble alkali and water are at a mass ratio of 100:10-2000:2-40:50-2000.
10. The process according to any of previous schemes, wherein the water-soluble alkali is a template agent for synthesizing the Ti—Si molecular sieve.
11. The process according to any of previous schemes, wherein the template agent for synthesizing the Ti—Si molecular sieve is selected from quaternary ammonium base.
12. The process according to any of previous schemes, wherein the organosilicon compound is selected from the compound as represented by formula (I)

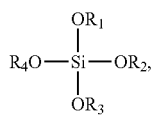

wherein each of $R_1$, $R_2$, $R_3$ and $R_4$ is $C_1$-$C_4$ alkyl.

13. The process according to any of previous schemes, wherein the Ti—Si molecular sieve is a MFI-type Ti—Si molecular sieve.

14. The process according to any of previous schemes, wherein the crystal grain of the Ti—Si molecular sieve is in hollow structure, the hollow structure has a cavity with radial length of 5-300 nm, the Ti—Si molecular sieve has a benzene adsorption capacity, measured at 25° C., P/P0=0.10, adsorption time=1 hour, of at least 70 mg/g, and there is a hysteresis loop between the adsorption isotherm and the desorption isotherm of the low temperature nitrogen adsorption of the Ti—Si molecular sieve.

15. The process according to any of previous schemes, wherein the molar ratio of dimethyl sulfide to the oxidant is 1:0.1-2.

16. The process according to any of previous schemes, wherein the oxidant is a peroxide.

17. The process according to any of previous schemes, wherein the oxidant is hydrogen peroxide.

18. The process according to any of previous schemes, wherein dimethyl sulfide and the solvent are at a mass ratio of 1:0.5-50.

19. The process according to any of previous schemes, wherein the solvent is selected from water, $C_1$-$C_6$alcohol, $C_3$-$C_8$ketone and $C_2$-$C_6$nitrile.

20. The process according to any of previous schemes, wherein the condition for contacting in step (2) includes: the temperature is 20-200° C.; and the pressure by gauge is 0.1-3 MPa.

21. The process according to any of previous schemes, wherein the contact in step (1) is conducted in the presence of γ-$Al_2O_3$.

22. The process according to any of previous schemes, wherein the weight ratio of hydrogen sulfide to γ-$Al_2O_3$ is 1:0.1-100.

23. The process according to any of previous schemes, wherein the molar ratio of hydrogen sulfide to methanol is 100-0.5:1.

24. The process according to any of previous schemes, wherein the contact in step (1) is conducted at 200-400° C.

The process of the present invention has a high dimethyl sulfide conversion, a high oxidant utility, and a good selectivity for dimethyl sulfoxide. In the process of the present invention, the Ti—Si molecular sieve as the catalyst for the step (2) is easy to separate from the product. In addition, the reaction condition of the process of the present invention is mild and easy to control, and the process is particularly suitable for large scale production.

DESCRIPTION OF DRAWINGS

The drawings are used to further explain the present invention and are a part of the application description. The drawings, together with the following specific mode for carrying out the invention, are used to explain the invention but do not limit the scope of the present invention in any way.

SPECIFIC MODE FOR CARRYING OUT THE INVENTION

Figure 1:
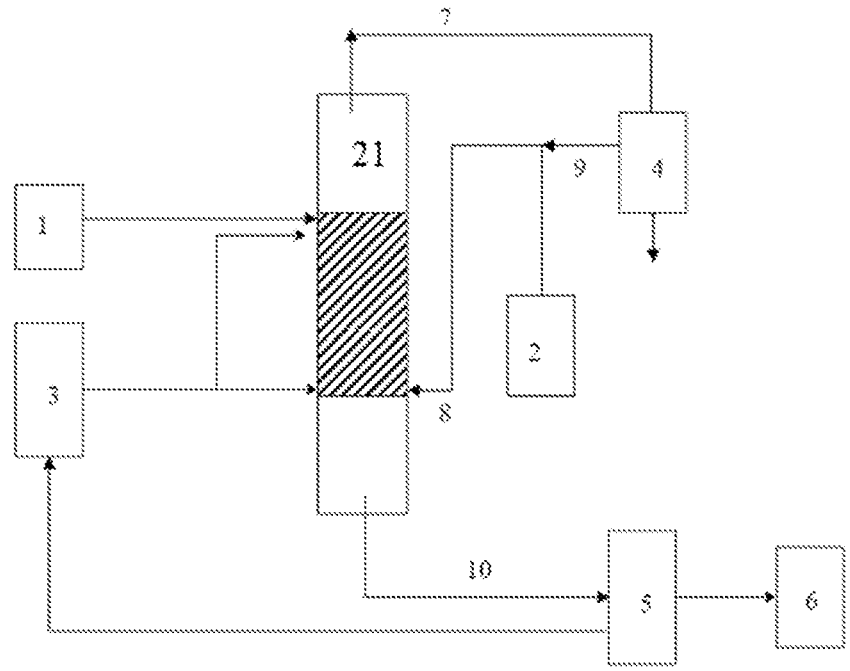
FIG. 1 illustrates a preferable embodiment according to the present invention, in which dimethyl sulfide and the oxidant are contacted to prepare a mixture containing dimethyl sulfoxide.

The present invention provides a process for producing dimethyl sulfoxide, which process comprises the following steps:

(1) contacting hydrogen sulfide with methanol to produce a mixture containing dimethyl sulfide, and separating dimethyl sulfide from the mixture; and (2) in the presence or absence of a solvent, contacting dimethyl sulfide with at least one oxidant and a catalyst to produce a mixture containing dimethyl sulfoxide, said catalyst comprises at least one Ti—Si molecular sieve.

Step (1)

According to the present invention, the process of contacting hydrogen sulfide and methanol to produce a mixture containing dimethyl sulfide is not particularly limited. Hydrogen sulfide and methanol can be contacted, in the presence of the catalyst that is conventionally used in the art and in a condition sufficient to produce dimethyl sulfide, to produce a mixture containing dimethyl sulfide. Specifically, the catalyst can be γ-$Al_2O_3$. According to the present invention, the used amount of γ-$Al_2O_3$ is not particularly limited, and can be suitably chosen according to the specific condition for contacting and the anticipated reaction rate. In general, the weight ratio of γ-$Al_2O_3$ to methanol can be 0.1-100:1, e.g. 5-50:1.

The used amounts of hydrogen sulfide and methanol are not particularly limited, and can be conventionally chosen. In general, the molar ratio of hydrogen sulfide to methanol can be 100-0.5:1, e.g. 1-5:1.

The condition for contacting hydrogen sulfide and methanol to produce dimethyl sulfide is not particularly limited, and can be suitably chosen according to the kind of the used catalyst. For example, in case that the catalyst is γ-$Al_2O_3$, the condition for contacting includes: the temperature can be 200-500° C., preferably 300-400° C.; the pressure by gauge can be 0.1-5 MPa, preferably 0.1-3 MPa, e.g. 0.1-1 MPa, or 0.3-0.5 MPa.

The kind of the reactor for contacting hydrogen sulfide and methanol is not particularly limited, and can be a batch reactor or a continuous reactor. For example, the contacting can be conducted in a fixed bed reactor.

According to the process of the present invention, dimethyl sulfide can be separated from a mixture containing dimethyl sulfide by any method conventionally used in the art. For example, dimethyl sulfide can be separated from a mixture containing dimethyl sulfide by flash distillation.

Step (2)

According to the process of the present invention, the contact of dimethyl sulfide and the oxidant is conducted in the presence of a catalyst containing at least one Ti—Si molecular sieve. If so, a higher dimethyl sulfide conversion, a higher oxidant utility and a higher selectivity for dimethyl sulfoxide can be accomplished; and the Ti—Si molecular sieve has a long lifetime with high activity, even if continuously used for a long period, it still shows a high catalytic activity.

The Ti—Si molecular sieve can be any conventional Ti—Si molecular sieve. For example, the Ti—Si molecular sieve can be selected from MFI-type Ti—Si molecular sieve (such as TS-1), MEL-type Ti—Si molecular sieve (such as TS-2), BEA-type Ti—Si molecular sieve (such as Ti-Beta), MWW-type Ti—Si molecular sieve (such as Ti-MCM-22), MOR-type Ti—Si molecular sieve (such as Ti-MOR), TUN-type Ti—Si molecular sieve (such as Ti-TUN), 2D hexagonal-type Ti—Si molecular sieve (such as Ti-MCM-41, Ti-SBA-15) and other-type Ti—Si molecular sieve (such as Ti-ZSM-48).

Preferably, the Ti—Si molecular sieve is selected from MFI-type Ti—Si molecular sieve, MEL-type Ti—Si molecular sieve and BEA-type Ti—Si molecular sieve. More preferably, the Ti—Si molecular sieve is MFI-type Ti—Si molecular sieve.

From the viewpoint of further improving the dimethyl sulfide conversion, the oxidant utility and the selectivity for dimethyl sulfoxide, the crystal grain of the Ti—Si molecular sieve is in hollow structure (i.e. with intra-particle voids). The hollow structure has a cavity with radial length of 5-300 nm. The Ti—Si molecular sieve has a benzene adsorption capacity, measured at 25° C., P/P0=0.10, adsorption time=1 hr, of at least 70 mg/g. There is a hysteresis loop between the adsorption isotherm and the desorption isotherm of the nitrogen adsorption of the Ti—Si molecular sieve at low temperature. In the present invention, the Ti—Si molecular sieve having this structure is named as the hollow Ti—Si molecular sieve. Furthermore, the catalyst containing the hollow Ti—Si molecular sieve has a longer lifetime with high activity. The hollow Ti—Si molecular sieve can be commercially available (for example, commercially available Hunan Jianchang Petrochemical Co., Ltd., HTS), or can be also prepared according to the disclosure of CN1132699C.

According to the process of the present invention, the used amount of the catalyst is not particularly limited, and can be suitably chosen according to the manner of contacting dimethyl sulfide and the oxidant with the catalyst, so that the content of the Ti—Si molecular sieve as the active component in the catalyst can meet the use requirement. Specifically, in case that the Ti—Si molecular sieve, the oxidant and dimethyl sulfide are made into slurry to contact, based on the total weight of the streams in the reactor, the content of the catalyst is 1-50 wt %, preferably 2-30% or the mass ratio of dimethyl sulfide and the catalyst can be 0.1-100:1, e.g. 2-50:1; in case that the catalyst is made into the catalyst bed, and the oxidant and dimethyl sulfide are passed through the catalyst bed to contact (i.e., the contact is performed in a fixed bed reactor), the weight hourly space velocity of dimethyl sulfide can be 0.1-10000 h$^{-1}$, preferably 0.1-1000 h$^{-1}$, more preferably 0.5-100 h$^{-1}$, most preferably 1-10 h$^{-1}$.

The catalyst can be an unshaped catalyst or a shaped catalyst. The preparation of the shaped catalyst can be conducted with any method conventionally used in the art, and is not particularly limited. Specifically, in case that the catalyst is the shaped catalyst, said catalyst contains the support and the Ti—Si molecular sieve. According to the present invention, the contents of the support and the Ti—Si molecular sieve in the catalyst are not particularly limited, provided that the content of the support is sufficient for the Ti—Si molecular sieve to be shaped and have certain intensity, and the content of the Ti—Si molecular sieve is sufficient to achieve the catalysis. In general, based on the total amount of the catalyst, the content of the Ti—Si molecular sieve can be 1-99 wt %, the content of the support can be 1-99 wt %. From the viewpoint of making a balance between the catalyst intensity and the catalytic activity, based on the total amount of the catalyst, the content of the Ti—Si molecular sieve preferably is 5-95 wt %, the content of the support preferably is 5-95 wt %.

According to the present invention, the kind of the support is not particularly limited, and can be conventionally chosen. In general, the support can be a heat-resistant inorganic oxide and/or a silicate. The heat-resistant inorganic oxide refers to an inorganic oxide, which has a decomposition temperature of not less than 300° C. under an oxygen atmosphere or an oxygen-containing atmosphere (for example, the decomposition temperature is 300-1000° C.). The silicate refers to a compound formed of the Si element, the O element and metal element(s). The support, for example, can be one or more of alumina, silica, titania, magnesia, zirconia, thoria, berillia and clay. Preferably, the support is alumina and/or silica. More preferably, the support is silica.

The shaped catalyst can be obtained with any conventional method. For example, the Ti—Si molecular sieve and the support as feedstock are mixed and shaped, and the resulting shaped bodies are dried and optionally calcined to obtain the shaped catalyst. The support feedstock is selected from heat-resistant inorganic oxide, a precursor of heat-resistant inorganic oxide, silicate and a precursor of silicate. The precursor of heat-resistant inorganic oxide can be any substance capable of forming the heat-resistant inorganic oxide. For example, if the heat-resistant inorganic oxide is alumina, the precursor can be various hydrated alumina; if the heat-resistant inorganic oxide is silica, the precursor can be selected from various silica sol and organosiloxane.

The shaping method is not particularly limited, and can be any conventional shaping method, for example, extruding, spraying, rounding, tabletting or a combination thereof. The shaped catalyst can have various conventional shapes, for example, sphere, bar, ring, clover leaf, honeycomb or butterfly, preferably sphere.

The condition for drying and calcining is not particularly limited, and can be the conventional drying and calcining condition. Specifically, the condition for drying comprises: the temperature can be 80-250° C., the time can be 0.5-12 hours. The condition for calcining comprises: the temperature can be 350-600° C., the time can be 0.5-12 hours. The calcining is preferably conducted in an oxygen-containing atmosphere, said oxygen-containing atmosphere, for example, can be an air atmosphere or an oxygen atmosphere.

The particle size of the shaped catalyst is also not particularly limited, and can be suitably chosen according to the specific shape. Preferably, if the shaped catalyst is in sphere, the average particle size of the shaped catalyst can be 2-5000 microns, preferably 5-2000 microns, or 40-600 microns. The particle diameter is the volume-average particle size measured with a laser particle sizer.

According to the process of the present invention, the oxidant can be any conventional substance capable of oxidizing dimethyl sulfide to form dimethyl sulfoxide. Preferably, the oxidant is selected from peroxide (i.e, a compound having a —O—O— bond in the molecular structure). The peroxide can be hydrogen peroxide and/or organic peroxide. Its specific example can include but be not limited to hydrogen peroxide, t-butylhydrogen peroxide, cumyl peroxide, cyclohexyl hydrogen peroxide, peroxyacetic acid and peroxypropionic acid. Preferably, the oxidant is hydrogen peroxide, which can further reduce separation cost. The hydrogen peroxide can be any hydrogen peroxide that is conventionally used in the art and present in various form.

From the viewpoint of further enhancing the safety of the process of the present invention, it is preferable that hydrogen peroxide present in form of an aqueous solution is used in the process of the present invention. According to the process of the present invention, in case that the hydrogen peroxide is provided in form of an aqueous solution, the concentration of the aqueous hydrogen peroxide solution can be any conventional concentration in the art, for example, 20-80 wt %. The aqueous hydrogen peroxide solution, having a concentration meeting the above requirement, can be formulated by the conventional method, or can be commercially available, for example, can be 30 wt % of hydrogen peroxide solution, 50 wt % of hydrogen peroxide solution or 70 wt % hydrogen peroxide solution, which can be commercially available.

The used amount of the oxidant can be conventionally chosen and is not particularly limited. In general, the molar ratio of dimethyl sulfide to the oxidant can be 1:0.1-2, preferably 1:0.3-2, more preferably 1:0.8-2.

According to the process of the present invention, from the viewpoint of further improving the mixing degree of various reactants in the reaction system, strengthening the diffusion, and adjusting the reaction intensity in a more convenient manner, it is preferable that the contact of dimethyl sulfide and at least one oxidant is conducted in the presence of at least one solvent. The kind of solvent is not particularly limited. In general, the solvent can be selected from water, $C_1$-$C_8$alcohol, $C_3$-$C_8$ketone and $C_2$-$C_8$nitrile, preferably water, $C_1$-$C_6$alcohol, $C_3$-$C_6$ketone and $C_2$-$C_7$nitrile. The specific example of the solvent can include, but not limited to: water, methanol, ethanol, n-propanol, isopropanol, tert-butyl alcohol, isobutyl alcohol, acetone, butanone, acetonitrile, propionitrile and benzyl cyanide. Preferably, the solvent is selected from water, acetone, methanol, benzyl cyanide and tert-butyl alcohol. From the viewpoint of further improving the environmental friendship of the process of the present invention, more preferably, the solvent is water. In addition, it is surprisingly found that in comparison with the organic solvent, the use of water as solvent can obtain higher dimethyl sulfide conversion, higher oxidant utility and higher selectivity for dimethyl sulfoxide. Water, as the solvent, can be of various sources, for example, the added water; in case that the oxidant is hydrogen peroxide present in the form of hydrogen peroxide solution, water present in the hydrogen peroxide solution. The used amount of the solvent is not particularly limited, and can be conventionally chosen. In general, the mass ratio of dimethyl sulfide to the solvent can be 1:0.5-50, preferably 1:1-20.

According to the process of the present invention, the condition for contacting dimethyl sulfide and at least one oxidant with the catalyst is not particularly limited. In general, the condition for contacting includes: the temperature can be 0-120° C., e.g. 0-100° C., or 20-80° C.; the pressure by gauge can be 0.1-3 MPa, e.g. 0.1-1.5 MPa.

According to the process of the present invention, the contacting of dimethyl sulfide and the oxidant with the catalyst can be conducted in various reactors conventionally used in the art. For example, the batch reactor can be used, or the continuous reactor can also be used. There is no particular limitation. The example of the reactor includes the slurry reactor and the catalytic distillation reactor. The feeding manner can also be any manner well known to the person skilled in the art.

In a preferable embodiment of the present invention, in the catalytic distillation reactor having at least one reaction zone, dimethyl sulfide and at least one oxidant are contacted in the reaction zone, the stream containing the unreacted dimethyl sulfide is obtained at the top of the catalytic distillation reactor, the dimethyl sulfoxide-containing stream is obtained at the bottom of the catalytic distillation reactor, the reaction zone is loaded with the catalyst. The reaction of dimethyl sulfide and the oxidant in the reaction zone being loaded with the Ti—Si molecular sieve as the active component of the catalyst in the catalytic distillation reactor under the catalytic distillation condition can thoroughly utilize the reaction potential heat, so that the oxidation product can be separated as the dimethyl sulfide feedstock is reacted, and therefore the higher dimethyl sulfide conversion, the higher oxidant utility and the higher selectivity for dimethyl sulfoxide can be obtained, while the subsequent separation cost can also be saved. Therefore the energy is saved and the consumption is reduced.

In the embodiment of the catalytic distillation reactor, the feeding of dimethyl sulfide and the oxidant to the reaction zone is not particularly limited. Preferably, the catalytic distillation reactor comprises the first feeding port and the second feeding port, the oxidant is fed from the first feeding port to the reaction zone, dimethyl sulfide is fed from the second feeding port to the reaction zone, the theoretical column plate number from the first feeding port to the bottom of the reaction zone is T1, the theoretical column plate number from the second feeding port to the bottom of the reaction zone is T2, T1>T2. More preferably, the theoretical column plate number of the reaction zone is T, the ratio of T1 to T as percent is 50-100%, the ratio of T2 to T as percent is 10-80%. Further preferably, the ratio of T1 to T as percent is 80-100%, the ratio of T2 to T as percent is 10-30%.

According to the present invention, the theoretical column plate number of the reaction zone is not particularly limited, can be conventionally chosen. Preferably, the theoretical column plate number of the reaction zone can be 20-45, preferably 30-40.

In this preferable embodiment, the catalyst can be in any form suitable for being loaded in the reaction zone to form the catalyst bed. Preferably, the catalyst is the shaped catalyst. The shaped catalyst, for example, can be the shaped catalyst as described above.

Preferably, the preparation of the shaped catalyst comprises: under a hydrolysis reaction condition, at least one organosilicon compound capable of hydrolysis and at least one water-soluble alkali are contacted with water, the mixture obtained by the contacting is mixed with a Ti—Si molecular sieve, the resulting mixture containing the Ti—Si molecular sieve is shaped and calcined. The shaped catalyst, as obtained according to this embodiment, not only has a higher intensity and thus is more abrasion resistant, but also has a higher anti-crushing ability, the bed containing this catalyst has a higher anti-collapsing ability; and a higher dimethyl sulfoxide yield and a higher selectivity for dimethyl sulfoxide can be obtained.

The organosilicon compound, the water-soluble alkali and the Ti—Si molecular sieve are used in such amounts that the Ti—Si molecular sieve can be shaped. Water is used in such an amount that the hydrolysis reaction can smoothly proceed. From the viewpoint of further improving the anti-crushing intensity of the finally prepared shaped catalyst and the dimethyl sulfoxide yield and the selectivity for dimethyl sulfoxide, the mass ratio of Ti—Si molecular sieve, the organosilicon compound, the water-soluble alkali and water is preferably 100:10-2000:2-40:50-2000, e.g. 100:100-500: 5-40:50-500.

The organosilicon compound is not particularly limited, and can be any compound that has a hydrolysable organic group on the silicon atom and can form silica by hydrolytic condensation. Specifically, the organosilicon compound can be selected from the siloxane represented by formula (I),

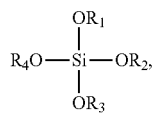

(I)

In formula I, each of $R_1$, $R_2$, $R_3$ and $R_4$ are $C_1$-$C_4$ alkyl. Said $C_1$-$C_4$ alkyl includes $C_1$-$C_4$ straight-chained alkyl and $C_3$-$C_4$ branch-chained alkyl, its specific example may include but is not limited to methyl, ethyl, n-propyl, iso-propyl, n-butyl, sec-butyl, isobutyl and t-butyl. Preferably, the organosilicon compound is selected from tetramethoxysilane, tetraethoxysilane, tetra(n-propoxy)silane, tetra(iso-propoxy)silane and tetra(n-butyl)silane.

The water-soluble alkali can be any conventional alkali that can be dissolved in water. For example, the water-soluble alkali can be a compound represented by formula $M(OH)_n$, wherein, M can be alkali metal, alkaline earth metal, $NH_4^+$ or quaternary ammonium group (i.e., a group formed from $NH_4^+$, in which hydrogen atom is substituted by a hydrocarbyl group, said hydrocarbyl group is preferably $C_1$-$C_{20}$ alkyl, $C_3$-$C_{20}$ cycloalkyl or $C_6$-$C_{20}$ aryl), n is an integer same as the chemical valance of M; the water-soluble alkali can also be any organic amine that can dissolve in water (preferably aliphatic amine) and/or alcohol amine (preferably fatty alcohol amine), its specific example can include but is not limited to ethylamine, propylamine and an isomer thereof, butylamine and an isomer thereof, butanediamine, monoethanolamine, diethanolamine and triethanolamine.

Preferably, the water-soluble alkali is a template agent for synthesizing the Ti—Si molecular sieve. The template agent for synthesizing the Ti—Si molecular sieve can be any compound that is used as the template agent when synthesizing the Ti—Si molecular sieve, preferably quaternary ammonium base. Said quaternary ammonium base can be conventionally chosen, e.g. can be the compound represented by formula II:

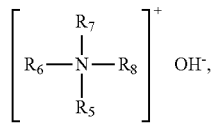

(II)

wherein, each of $R_5$, $R_6$, $R_7$ and $R_8$ are $C_1$-$C_{20}$ alkyl (including $C_1$-$C_{20}$ straight-chained alkyl and $C_3$-$C_{20}$ branch-chained alkyl), $C_3$-$C_{20}$ cycloalkyl or $C_6$-$C_{20}$ aryl. Preferably, each of $R_5$, $R_6$, $R_7$ and $R_8$ are $C_1$-$C_{10}$ alkyl (including $C_1$-$C_{10}$ straight-chained alkyl and $C_3$-$C_{10}$ branch-chained alkyl) and $C_3$-$C_{10}$ cycloalkyl. Further preferably, each of $R_5$, $R_6$, $R_7$ and $R_8$ are $C_1$-$C_6$ alkyl (including $C_1$-$C_6$ straight-chained alkyl and $C_3$-$C_6$ branch-chained alkyl). Specific example of said $C_1$-$C_{20}$ alkyl can include but is not limited to one or more of methyl, ethyl, n-propyl, iso-propyl, n-butyl, sec-butyl, isobutyl, t-butyl, n-pentyl, neo-pentyl, isopentyl, tert-pentyl, n-hexyl, n-octyl, n-nonyl, n-decyl, n-undecyl, n-dodecyl, n-tridecyl, n-tetradecyl, n-pentadecyl, n-hexadecyl, n-octadecyl and n-eicosyl. The example of $C_6$-$C_{20}$ aryl can include but is not limited to phenyl, naphthyl, 4-methylphenyl and 4-ethylphenyl. The example of $C_3$-$C_{20}$ cycloalkyl can include but is not limited to cyclopropyl, cyclopentyl, cyclohexyl, 4-methylcyclohexyl, 4-ethylcyclohexyl, 4-n-propyl-cyclohexyl and 4-n-butylcyclohexyl.

The example of said quaternary ammonium base can include but is not limited to tetra propyl ammonium hydroxide (including tetra n-propyl ammonium hydroxide and tetra iso-propyl ammonium hydroxide), tetra ethyl ammonium hydroxide, tetra methyl ammonium hydroxide and tetra butyl ammonium hydroxide (including tetra n-butyl ammonium hydroxide, tetra sec-butyl ammonium hydroxide, tetra isobutyl ammonium hydroxide and tetra t-butyl ammonium hydroxide).

The hydrolysis reaction condition is not particularly limited, and can be conventionally chosen, provided that the organosilicon compound can be completely hydrolyzed. In general, the hydrolysis reaction condition includes: the temperature can be 20-100° C., the time can be 0.5-10 hours.

The shaping of the resulting mixture containing the Ti—Si molecular sieve and the condition for calcining are not particularly limited, and can be conventionally chosen, provided that the catalyst having a pre-determined shape can be obtained, for example, can be the shaping method and the calcining condition for the catalyst as described above.

According to the process of the present invention, the reaction zone can also be loaded with the packing. Loading the packing in the reaction zone can adjust the amount of the catalyst in the reaction zone, and thus adjust the reaction rate and the reaction zone throughput. The loading amount of the packing can be suitably selected according to the anticipated reaction rate and the reaction zone throughput, provided that the specific use requirement can be met. In general, based on the total amount of the packing and the catalyst, the content of the catalyst in the reaction zone can be 30-95 wt %, preferably 30-70 wt %.

According to the present invention, the kind of the packing is not particularly limited, can be any conventional packing, e.g. can be selected from rasching ring, pall ring, cascade ring, arc saddle, intalox saddle and metal intalox. The specific example of the packing can be θ ring and/or β ring.

In the case that the packing is loaded in the reaction zone, the packing and the catalyst can be loaded in the reaction zone in a form of a mixture of the packing and the catalyst; or the catalyst bed(s) formed of the catalyst and the packing bed(s) formed of the packing are loaded in the reaction zone alternatively with each other; or a combination thereof.

From the viewpoint of enhancing the anti-collapsing ability of the catalyst bed and obtaining a higher dimethyl sulfoxide yield, it is preferable that the catalyst bed(s) formed of the catalyst and the packing bed(s) formed of the packing are loaded in the reaction zone alternatively with each other, so that the reaction zone is divided several sections (i.e. several catalyst bed(s) are located in the reaction zone, two adjacent catalyst beds are spaced by a packing bed). In this case, the height of each catalyst bed and the height of each packing bed can be conventionally chosen. In general, the ratio of the height of a catalyst bed to the height of a packing bed that is conterminous to that catalyst bed can be 1:0.1-10.

In the case that the contacting of dimethyl sulfide and the oxidant with the catalyst is conducted in the reaction zone in the presence of at least one solvent, various methods conventionally used in the art can be applied to feed the solvent to the reaction zone, so that the contact of dimethyl sulfide and the oxidant is conducted in the presence of the solvent. For example, the solvent can be fed to the reaction zone from the upper part of the reaction zone or from the lower part of the reaction zone. Upon feeding the solvent to the reaction zone from the lower part of the reaction zone, said solvent is preferably fed at the same location as dimethyl sulfide to the reaction zone. More preferably, the solvent and the oxidant are fed to the reaction zone through the same feeding port.

In case that the contacting of dimethyl sulfide and the oxidant with the catalyst is conducted in the catalytic distillation reactor, the condition for contacting is not particularly limited, provided that dimethyl sulfide can be oxidized to dimethyl sulfoxide, and the formed dimethyl sulfoxide can be separated from the unreacted dimethyl sulfide. In general, the condition for contacting includes: the temperature can be 20-200° C., preferably 30-180° C., more preferably 30-120° C.; the reflux ratio can be 1:1 or more (e.g. 1-100:1), preferably 2:1 or more (e.g. 2-20:1); the weight hourly space velocity of dimethyl sulfide can be 0.1-10000 $h^{-1}$, preferably 1-1000 $h^{-1}$, more preferably 2-20 $h^{-1}$; the pressure by gauge in the catalytic distillation reactor can be 0.1-3 MPa, preferably 0.1-1.5 MPa. The reflux ratio means the ratio of the mass of the stream returning to the reaction zone to the mass of the stream that is obtained from the reaction zone as the product.

The heating to the reaction zone can be conducted with various methods conventionally used in the art, so that the temperature in the reaction zone is sufficient for the reaction between the dimethyl sulfide and the oxidant, and is sufficient for the distillation.

The process of the present invention can be conducted in the catalytic distillation reactor conventionally used in the art, in which the catalytic reaction and the distillation separation can be conducted at the same time. In general, the catalytic distillation reactor can have a distillation zone, a reaction zone and a stripping zone, and the reaction zone is located between the distillation zone and the stripping zone. The catalyst can be loaded in the reaction zone according to various methods conventionally used in the art. Dimethyl sulfide and the oxidant are contacted with the catalyst in the reaction zone of the catalytic distillation reactor, the stream containing the unreacted dimethyl sulfide is obtained from the top of the catalytic distillation reactor, and the dimethyl sulfoxide-containing stream is obtained at the bottom of the catalytic distillation reactor.

The stream containing the unreacted dimethyl sulfide can be subjected to the separation method conventionally used in the art to obtain dimethyl sulfide. The obtained dimethyl sulfide is again fed to the reaction zone to contact with the oxidant and the catalyst. For example, dimethyl sulfide can be separated from the stream containing the unreacted dimethyl sulfide by distillation.

According to the process of the present invention, the obtained dimethyl sulfoxide-containing stream can be subjected to the separation method conventionally used in the art to obtain dimethyl sulfoxide. For example, dimethyl sulfoxide can be separated from a mixture containing dimethyl sulfoxide by rectification.

Hereinafter, with reference to the figures, the present invention will be illustrated.

FIG. 1 illustrates an embodiment, wherein dimethyl sulfide and the oxidant are contacted with the catalyst in the reaction zone of the catalytic distillation reactor, to obtain the stream containing the unreacted dimethyl sulfide and the dimethyl sulfoxide-containing stream. As shown in FIG. 1, hydrogen peroxide in a form of hydrogen peroxide solution is used as the oxidant. The hydrogen peroxide storage tank 1 is connected to the upper part of the reaction zone (i.e., the shadow in FIG. 1) of the catalytic distillation reactor 21. Hydrogen peroxide solution is fed to the upper part of the reaction zone. The solvent storage tank 3 is connected to the upper or lower part of the reaction zone. The solvent is fed to the upper or lower part of the reaction zone. The dimethyl sulfide storage tank 2 is connected to the lower part of the reaction zone. Dimethyl sulfide is fed to the lower part of the reaction zone (preferably, the solvent and hydrogen peroxide is fed through the same feeding port to the reaction zone). The condition in the reaction zone is adjusted so that the oxidant and dimethyl sulfide can be subjected to an oxidation reaction to form dimethyl sulfoxide, and the formed dimethyl sulfoxide and dimethyl sulfide are subjected to a distillation separation condition to obtain the dimethyl sulfoxide-containing stream 10 at the bottom of the catalytic distillation reactor 21, and the stream containing the unreacted dimethyl sulfide 7 at the top of the catalytic distillation reactor 21. The stream containing the unreacted dimethyl sulfide 7 is fed to the sulfide intermediate tank 4 to conduct a gas-liquid separation to obtain the dimethyl sulfide stream 9, which is fed to the sulfide storage tank 2. The dimethyl sulfoxide-containing stream 10 was fed to the solvent separation tank 5 to separate out the solvent and obtain the dimethyl sulfoxide-containing stream, which is fed to the product separation tank 6 to conduct the separation to obtain dimethyl sulfoxide.

Figure 2:
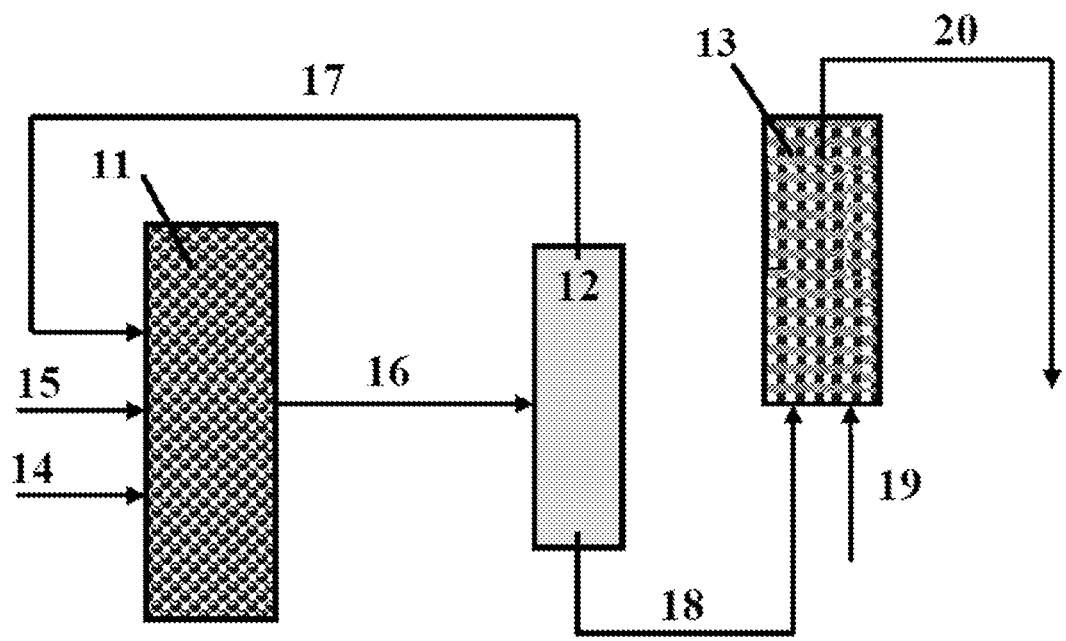
FIG. 2 illustrates a process for producing dimethyl sulfoxide according to the present invention.

FIG. 2 illustrates an embodiment of the process for producing dimethyl sulfoxide according to the present invention. As shown in FIG. 2, hydrogen sulfide 15 and methanol 14 are fed to the sulfide production reactor 11 to react and obtain a mixture containing dimethyl sulfide 16. The mixture containing dimethyl sulfide 16 is fed to the gas-liquid separator 12 to separate and obtain the gas-phase stream 17 containing unreacted hydrogen sulfide, and the liquid-phase stream containing methanol and dimethyl sulfide 18. The gas-phase stream 17 is sent back to the sulfide production reactor 11 to prepare dimethyl sulfide. The liquid-phase stream 18 and the oxidant 19 are fed to the oxidation reactor 13 to contact with the catalyst containing Ti—Si molecular sieve to obtain dimethyl sulfoxide. The obtained dimethyl sulfoxide-containing stream 20 is fed to the subsequent separation unit to conduct the separation. The oxidation reactor 13 preferably is a reactor in which the catalytic distillation can be conducted, so that dimethyl sulfide and the oxidant are contacted with the catalyst in which the Ti—Si molecular sieve is used as the active component in the reaction zone of the catalytic distillation reactor to obtain dimethyl sulfoxide.

EXAMPLES

Hereinafter, the present invention will be described in combination with Examples.

Unless indicated otherwise, the agents used in the Examples are chemical pure agents, which are commercially available.

In the following examples, the used hollow Ti—Si molecular sieve was prepared according to the method disclosed in Chinese Patent CN1132699C. By analysis, this Ti—Si molecular sieve was MFI-type; there was a hysteresis loop between the adsorption isotherm and the desorption isotherm of the low temperature nitrogen adsorption of the Ti—Si molecular sieve; the crystal grain was a hollow crystal grain and had a cavity with radial length of 15-180 nm; and the Ti—Si molecular sieve sample had a benzene adsorption capacity, measured at 25° C., P/P0=0.10, adsorption time=1 hr, of 78 mg/g. Its titania content was 2.5 wt %.

In the Examples, the used Ti—Si molecular sieve TS-1 was prepared according to the method as disclosed in Journal of Natural Gas Chemistry, 2001, 10(4): 295-307, its titania content was 2.5 wt %.

In the Examples, the used hydrogen peroxide solutions were respectively 27.5 wt % of hydrogen peroxide solution and 50 wt % of hydrogen peroxide solution, commercially available.

In the Examples, the used packing θ ring was commercially available from Kaimeite Chemical Engineering Technology Ltd, TianJin, China.

In the Examples, the average particle size was determined with Mastersizer 2000 type laser particle sizer, commercially available from Malvern Instruments Ltd. UK, wherein average particle size was the volume-average particle size.

In the Examples, the pressure was expressed by gauge.

In the Examples, the composition of a mixture was measured by gas chromatography, and quantified by corrected normalization, the dimethyl sulfide conversion, the selectivity for dimethyl sulfoxide and the hydrogen peroxide utility were calculated based on the following equations:

$$X_{sulfide} = \frac{m^0_{sulfide} - m_{sulfide}}{m^0_{sulfide}} \times 100\% \quad \text{(III)}$$

wherein, $X_{sulfide}$ represented the dimethyl sulfide conversion,
$m^0_{sulfide}$ represented the mass of the added dimethyl sulfide;
$m_{sulfide}$ represented the mass of the unreacted dimethyl sulfide.

$$S_{sulfoxide} = \frac{n_{sulfoxide}}{n^0_{sulfide} - n_{sulfide}} \times 100\% \quad \text{(IV)}$$

wherein, $S_{sulfoxide}$ represented the selectivity for dimethyl sulfoxide;
$n^0_{sulfide}$ represented the mole of the added dimethyl sulfide;
$n_{sulfide}$ represented the mole of the unreacted dimethyl sulfide;
$n_{sulfide}$ represented the mole of the obtained dimethyl sulfoxide.

$$U_{H_2O_2} = \frac{n_{sulfoxide}}{n^0_{H_2O_2} - n_{H_2O_2}} \times 100\% \quad \text{(V)}$$

wherein, $U_{H_2O_2}$ represented the hydrogen peroxide utility;
$n^0_{H_2O_2}$ represented the mole of the added hydrogen peroxide;
$n_{H_2O_2}$ represented the mole of the unreacted hydrogen peroxide;
$n_{sulfoxide}$ represented the mole of the obtained dimethyl sulfoxide.

Working examples 1-20 were to illustrate the process for producing dimethyl sulfide.

Working examples 1-4 were conducted according to the process flow as shown in FIG. 2, wherein hydrogen sulfide and methanol were reacted to produce dimethyl sulfide in a fixed reactor; and dimethyl sulfide and the oxidant were contacted with the catalyst in a slurry reactor to produce dimethyl sulfoxide.

Working Example 1

(1) Preparation and separation of dimethyl sulfide

At 380° C. and 0.5 MPa, hydrogen sulfide and methanol (molar ratio=1:1) were mixed with γ-Al$_2$O$_3$ as the catalyst, and reacted. The weight ratio of the catalyst/methanol was 15:1. The obtained mixture was filtered to obtain a mixture containing dimethyl sulfide, which was subjected to a gas-liquid separation to obtain dimethyl sulfide.

(2) The hollow Ti—Si molecular sieve was placed in a methanol solution containing hydrogen peroxide (wherein, hydrogen peroxide content=25 wt %). The mixture was stirred as slurry, and then added to the reactor via the catalyst port. Dimethyl sulfide prepared in step (1) was feed to the reaction.

Based on the total weight of the streams in the reactor,

The content of the catalyst was 15 wt %,

The molar ratio of methanol/hydrogen peroxide was 40:1,

The molar ratio of dimethyl sulfide/hydrogen peroxide was 2:1, the weight hourly space velocity of dimethyl sulfide was 1.5 h$^{-1}$, The pressure at the reactor outlet was 2.0 MPa, The temperature in the reactor was 45° C., The reaction was continuously conducted for 100 hours.

The slurry output from the reactor was subjected to a solid-liquid separation to obtain a liquid phase containing dimethyl sulfoxide.

During the reaction, the sampling was made via the sampling port every 2 hours, wherein The hydrogen peroxide conversion was >98%, The averaged selectivity for dimethyl sulfoxide was 93%.

Working Example 2

(1) Preparation and separation of dimethyl sulfide

At 350° C. and 0.3 MPa, hydrogen sulfide and methanol (molar ratio=5:1) were mixed with γ-Al$_2$O$_3$ as the catalyst, and reacted. The weight ratio of the catalyst/methanol was 5:1. The obtained mixture was filtered to obtain a mixture containing dimethyl sulfide, which was subjected to a gas-liquid separation to obtain dimethyl sulfide.

(2) The hollow Ti—Si molecular sieve was placed in a methanol solution containing hydrogen peroxide (wherein, hydrogen peroxide content=25 wt %). The mixture was stirred as slurry, and then added to the reactor via the catalyst port. Dimethyl sulfide prepared in step (1) was feed to the reaction.

Based on the total weight of the streams in the reactor,

The content of the catalyst was 20 wt %,

The molar ratio of methanol/hydrogen peroxide was 40:1,

The molar ratio of dimethyl sulfide/hydrogen peroxide was 2:1,

The weight hourly space velocity of dimethyl sulfide was 0.5 h$^{-1}$,

The pressure at the reactor outlet was 2.0 MPa,

The temperature in the reactor was 60° C.,

The reaction was continuously conducted for 200 hours.

The slurry output from the reactor was subjected to a solid-liquid separation to obtain a liquid phase containing dimethyl sulfoxide.

During the reaction, the sampling was made via the sampling port every 2 hours, wherein
The hydrogen peroxide conversion was >98%,
The averaged selectivity for dimethyl sulfoxide was 95%.

Working Example 3

(1) Preparation and separation of dimethyl sulfide
At 320° C. and 0.2 MPa, hydrogen sulfide and methanol (molar ratio=5:1) were mixed with γ-$Al_2O_3$ as the catalyst, and reacted. The weight ratio of the catalyst/methanol was 50:1. The obtained mixture was filtered to obtain a mixture containing dimethyl sulfide, which was subjected to a gas-liquid separation to obtain dimethyl sulfide.
(2) The hollow Ti—Si molecular sieve was placed in a methanol solution containing hydrogen peroxide (wherein, hydrogen peroxide content=25 wt %). The mixture was stirred as slurry, and then added to the reactor via the catalyst port. Dimethyl sulfide prepared in step (1) was feed to the reaction.
Based on the total weight of the streams in the reactor,
The content of the catalyst was 15 wt %,
The molar ratio of methanol/hydrogen peroxide was 40:1,
The molar ratio of dimethyl sulfide/hydrogen peroxide was 2:1,
The weight hourly space velocity of dimethyl sulfide was 5.5 $h^{-1}$,
The pressure at the reactor outlet was 2.5 MPa,
The temperature in the reactor was 45° C.,
The reaction was continuously conducted for 150 hours.
The slurry output from the reactor was subjected to a solid-liquid separation to obtain a liquid phase containing dimethyl sulfoxide.
During the reaction, the sampling was made via the sampling port every 2 hours, wherein
The hydrogen peroxide conversion was >97%,
The averaged selectivity for dimethyl sulfoxide was 94%.

Working Example 4

This example repeated Working example 1 except for using the Ti—Si molecular sieve TS-1 to replace the hollow Ti—Si molecular sieve.
During the reaction, the sampling was made via the sampling port every 2 hours, wherein
The hydrogen peroxide conversion was >95%,
The averaged selectivity for dimethyl sulfoxide was 90%.
Working examples 5-20 were conducted according to the process flow as shown in FIG. 1 to oxidize dimethyl sulfide, wherein step (1) of Working example 1 was repeated to prepare and separate dimethyl sulfide; then in the catalytic distillation reactor having one the reaction zone, dimethyl sulfide and the oxidant were contacted with the catalyst, wherein the catalytic distillation reactor comprised the distillation zone, the reaction zone and the stripping zone, the reaction zone was located between the distillation zone and the stripping zone, and no packing was loaded in both the distillation zone and the stripping zone.
Preparation Example 1-9 were used to prepare the catalysts used in Working example 5-20.

Preparation Example 1

At 1 atm and 40° C., tetraethyl silicate was added to an aqueous tetrapropylammonium hydroxide solution. After stirring for 2 hours, the hollow Ti—Si molecular sieve was added, the stirring was continued for 1 hour. The mass ratio of the hollow Ti—Si molecular sieve:tetraethyl silicate:tetrapropylammonium hydroxide:water was 100:350:5:120. The resulting mixture was granulated by rounding, calcined at 550° C. for 5 hours to produce sphere catalyst having an average particle size of 5 microns.

Preparation Example 2

Repeating Preparation Example 1, except that, the mass ratio of the hollow Ti—Si molecular sieve:tetraethyl silicate:tetrapropylammonium hydroxide:water was 100:100:10:50, and the granulation by rounding to produce sphere catalyst having an average particle size of 100 microns.

Preparation Example 3

Repeating Preparation Example 1, except that, the mass ratio of the hollow Ti—Si molecular sieve:tetraethyl silicate:tetrapropylammonium hydroxide:water was 100:200:40:500, and the granulation by rounding to produce sphere catalyst having an average particle size of 2000 microns.

Preparation Example 4

Repeating Preparation Example 1, except that, the granulation by rounding to produce sphere catalyst having an average particle size of 500 microns.

Preparation Example 5

Repeating Preparation Example 1, except for replacing tetrapropylammonium hydroxide with tetraethylammonium hydroxide and replacing tetraethyl silicate with tetramethyl silicate.

Preparation Example 6

Repeating Preparation Example 1, except that, the mass ratio of the hollow Ti—Si molecular sieve:tetraethyl silicate:tetrapropylammonium hydroxide:water was 100:300:50:2000.

Preparation Example 7

Repeating Preparation Example 1, except for replacing the hollow Ti—Si molecular sieve with the Ti—Si molecular sieve TS-1.

Preparation Example 8

The hollow Ti—Si molecular sieve and silica sol ($SiO_2$ content: 40 wt %) were mixed at a weight ratio of 100:250 and slurried. The resulting slurry was granulated by spraying to produce sphere catalyst having an average particle size of 50 microns.

Preparation Example 9

Repeating Preparation Example 1, except for replacing tetrapropylammonium hydroxide with an aqueous NaOH solution.

Working Example 5

Dimethyl sulfide, hydrogen peroxide solution (having a concentration of 27.5 wt %) and acetone, at a mass ratio of 1:1.72:15 were fed from the feeding ports of the reaction zone, wherein dimethyl sulfide was fed from the second feeding port, hydrogen peroxide solution and acetone were fed from the first feeding port, the temperature of the reaction zone was 47±3° C., the reaction zone pressure was 0.15±0.02 MPa, the weight hourly space velocity of dimethyl sulfide was 2 h$^{-1}$, the reflux ratio in the reaction zone was 5:1, the total theoretical column plate number of the reaction zone was 35, the theoretical column plate number from the first feeding port to the reaction zone bottom was 30, the theoretical column plate number from the second feeding port to the reaction zone bottom was 10, the reaction zone was loaded with The catalyst made in Preparation Example 1 and θ ring (based on the total weight of the catalyst and the packing, the content of θ ring was 40 wt %, a mixture of θ ring and the catalyst was loaded in the reaction zone). The sampling and analysis was made after 12 hours stable run, and the calculation was made for the dimethyl sulfide conversion, the selectivity for dimethyl sulfoxide and the hydrogen peroxide utility. The results were listed in Table 1.

Working Example 6

Dimethyl sulfide, hydrogen peroxide solution (having a concentration of 27.5 wt %) and benzyl cyanide, at a mass ratio of 1:3.44:8.89 were fed from the feeding ports of the reaction zone, wherein dimethyl sulfide was fed from the second feeding port, hydrogen peroxide solution and benzyl cyanide were fed from the first feeding port, the temperature of the reaction zone was 70±5° C., the reaction zone pressure was 0.35±0.05 MPa, the weight hourly space velocity of dimethyl sulfide was 8 h$^{-1}$, the reflux ratio in the reaction zone was 8:1, the total theoretical column plate number of the reaction zone was 35, the theoretical column plate number from the first feeding port to the reaction zone bottom was 30, the theoretical column plate number from the second feeding port to the reaction zone bottom was 10, the reaction zone was loaded with The catalyst made in Preparation Example 2 and θ ring (based on the total weight of the catalyst and the packing, the content of θ ring was 30 wt %, a mixture of θ ring and the catalyst was loaded in the reaction zone). The sampling and analysis was made after 8 hours stable run, and the calculation was made for the dimethyl sulfide conversion, the selectivity for dimethyl sulfoxide and the hydrogen peroxide utility. The results were listed in Table 1.

Working Example 7

Dimethyl sulfide, hydrogen peroxide solution (having a concentration of 50 wt %) and tert-butyl alcohol, at a mass ratio of 1:1.72:10 were fed from the feeding ports of the reaction zone, wherein dimethyl sulfide was fed from the second feeding port, hydrogen peroxide solution and tert-butyl alcohol were fed from the first feeding port, the temperature in the reaction zone was 110±5° C., the pressure in the reaction zone was 0.50±0.02 MPa, the weight hourly space velocity of dimethyl sulfide was 5 h$^{-1}$, the reflux ratio in the reaction zone was 3:1, the total theoretical column plate number of the reaction zone was 35, the theoretical column plate number from the first feeding port to the reaction zone bottom was 30, the theoretical column plate number from the second feeding port to the reaction zone bottom was 10, the reaction zone was loaded with the catalyst made in Preparation Example 3 and θ ring (based on the total weight of the catalyst and the packing, the content of θ ring was 10 wt %, a mixture of θ ring and the catalyst was loaded in the reaction zone). The sampling and analysis was made after 18 hours stable run, and the calculation was made for the dimethyl sulfide conversion, the selectivity for dimethyl sulfoxide and the hydrogen peroxide utility. The results were listed in Table 1.

Working Example 8

Dimethyl sulfide was oxidized in the same manner as Working example 5, except that, the catalyst was the catalyst made in Preparation Example 4. The conversion of the obtained dimethyl sulfide, the selectivity for dimethyl sulfoxide and the hydrogen peroxide utility was listed in Table 1.

Working Example 9

Dimethyl sulfide was oxidized in the same manner as Working example 5, except that, the catalyst was the catalyst made in Preparation Example 5. The conversion of the obtained dimethyl sulfide, the selectivity for dimethyl sulfoxide and the hydrogen peroxide utility was listed in Table 1.

Working Example 10

Dimethyl sulfide was oxidized in the same manner as Working example 5, except that, the catalyst was the catalyst made in Preparation Example 6. The conversion of the obtained dimethyl sulfide, the selectivity for dimethyl sulfoxide and the hydrogen peroxide utility was listed in Table 1.

Working Example 11

Dimethyl sulfide was oxidized in the same manner as Working example 5, except that, the catalyst was the catalyst made in Preparation Example 7. The conversion of the obtained dimethyl sulfide, the selectivity for dimethyl sulfoxide and the hydrogen peroxide utility was listed in Table 1.

Working Example 12

Dimethyl sulfide was oxidized in the same manner as Working example 5, except that, the catalyst was the catalyst made in Preparation Example 8. The conversion of the obtained dimethyl sulfide, the selectivity for dimethyl sulfoxide and the hydrogen peroxide utility was listed in Table 1.

Working Example 13

Dimethyl sulfide was oxidized in the same manner as Working example 5, except that, the solvent was butanone. The conversion of the obtained dimethyl sulfide, the selectivity for dimethyl sulfoxide and the hydrogen peroxide utility was listed in Table 1.

Working Example 14

Dimethyl sulfide was oxidized in the same manner as Working example 5, except that, the solvent was acetic acid. The conversion of the obtained dimethyl sulfide, the selectivity for dimethyl sulfoxide and the hydrogen peroxide utility was listed in Table 1.

Working Example 15

Dimethyl sulfide, hydrogen peroxide solution (having a concentration of 50 wt %) and water, at a mass ratio of 2:3:1 were fed from the feeding ports of the reaction zone, wherein dimethyl sulfide was fed from the second feeding port, hydrogen peroxide solution and water were fed from the first feeding port, the temperature in the reaction zone was 39±2° C., the pressure in the reaction zone was 0.10±0.02 MPa, the weight hourly space velocity of dimethyl sulfide was 4 $h^{-1}$, the reflux ratio in the reaction zone was 10:1, the total theoretical column plate number of the reaction zone was 35, the theoretical column plate number from the first feeding port to the reaction zone bottom was 30, the theoretical column plate number from the second feeding port to the reaction zone bottom was 10, the reaction zone was loaded with the catalyst made in Preparation Example 1 (i.e., the reaction zone was not loaded with the packing). The sampling and analysis was made after 15 hours stable run, and the calculation was made for the dimethyl sulfide conversion, the selectivity for dimethyl sulfoxide and the hydrogen peroxide utility. The results were listed in Table 1.

Working Example 16

Dimethyl sulfide was oxidized in the same manner as Working example 5, except that, the used catalyst was the catalyst prepared in the Preparation Example 9. The conversion of the obtained dimethyl sulfide, the selectivity for dimethyl sulfoxide and the hydrogen peroxide utility was listed in Table 1.

Working Example 17

Dimethyl sulfide was oxidized in the same manner as Working example 5, except that, the column plate number from the first feeding port to the column bottom was 18. The conversion of the obtained dimethyl sulfide, the selectivity for dimethyl sulfoxide and the hydrogen peroxide utility was listed in Table 1.

Working Example 18

Dimethyl sulfide was oxidized in the same manner as Working example 5, except that, the column plate number between the second feeding port and the column bottom was 5. The conversion of the obtained dimethyl sulfide, the selectivity for dimethyl sulfoxide and the hydrogen peroxide utility was listed in Table 1.

Working Example 19

Dimethyl sulfide was oxidized in the same manner as Working example 5, except that, acetone was replaced with the same amount of methanol. The conversion of the obtained dimethyl sulfide, the selectivity for dimethyl sulfoxide and the hydrogen peroxide utility was listed in Table 1.

Working Example 20

Dimethyl sulfide was oxidized in the same manner as Working example 5, except that, acetone was replaced with the same amount of water. The conversion of the obtained dimethyl sulfide, the selectivity for dimethyl sulfoxide and the hydrogen peroxide utility was listed in Table 1.

TABLE 1

| No. | Dimethyl sulfide conversion (%) | Selectivity for dimethyl sulfoxide (%) | Utility of hydrogen peroxide (%) |
| --- | --- | --- | --- |
| Working example 5 | 85 | 93 | 88 |
| Working example 6 | 83 | 92 | 85 |
| Working example 7 | 87 | 90 | 89 |
| Working example 8 | 90 | 94 | 91 |
| Working example 9 | 84 | 92 | 87 |
| Working example 10 | 89 | 90 | 92 |
| Working example 11 | 78 | 92 | 86 |
| Working example 12 | 74 | 91 | 88 |
| Working example 13 | 82 | 90 | 89 |
| Working example 14 | 70 | 86 | 77 |
| Working example 15 | 92 | 98 | 94 |
| Working example 16 | 72 | 89 | 77 |
| Working example 17 | 81 | 92 | 84 |
| Working example 18 | 88 | 95 | 92 |
| Working example 19 | 92 | 97 | 94 |
| Working example 20 | 90 | 95 | 92 |

It can be seen from Table 1 that the contacting of dimethyl sulfide and the oxidant with the catalyst containing the Ti—Si molecular sieve in the reaction zone of the catalytic distillation reactor can not only obtain high dimethyl sulfide conversion and high selectivity for dimethyl sulfoxide, as well as high hydrogen peroxide utility, but also can separate the product as the reaction proceeds, which effectively utilize the heat produced in the oxidation system and save the energy consumption.

The invention claimed is:

1. A process for producing dimethyl sulfoxide, comprising:
    (1) contacting hydrogen sulfide with methanol to produce a mixture containing dimethyl sulfide, and separating dimethyl sulfide from the mixture; and
    (2) in the presence of a solvent, contacting a dimethyl sulfide feed obtained in step (1) with at least one oxidant and a catalyst to produce a mixture containing dimethyl sulfoxide,
    wherein said catalyst comprises at least one Ti—Si molecular sieve, and wherein the solvent is water.

2. The process of claim 1, wherein, in step (2), the contacting of the dimethyl sulfide feed with the at least one oxidant and the catalyst is conducted in a reaction zone of a catalytic distillation reactor, a mixture containing an unreacted dimethyl sulfide is obtained at the top of the catalytic distillation reactor, the mixture containing dimethyl sulfoxide is obtained at the bottom of the catalytic distillation reactor, and the reaction zone is loaded with the catalyst.

3. The process of claim 2, wherein the oxidant and the solvent are fed through the first feeding port to the reaction zone; the dimethyl sulfide feed is fed through the second feeding port to the reaction zone; a theoretical column plate number from the first feeding port to the bottom of the reaction zone is T1, the theoretical column plate number from the second feeding port to the bottom of the reaction zone is T2, and T1>T2.

4. The process of claim 3, wherein the theoretical column plate number of the reaction zone is T, a ratio of T1 to T expressed in percentage is 50-100%, the ratio of T2 to T expressed in percentage is 10-80%.

5. The process of claim 4, wherein the ratio of T1 to T expressed in percentage is 80-100%, the ratio of T2 to T expressed in percentage is 10-30%.

6. The process of claim 1, wherein, in step (2), the dimethyl sulfide feed and the catalyst are in contact in a batch reactor at a mass ratio of 0.1-100:1; or the dimethyl sulfide feed and the catalyst are in contact in a fixed bed reactor at a weight hourly space velocity of the dimethyl sulfide feed of 0.1-10000 h$^{-1}$.

7. The process of claim 1, wherein said catalyst comprises the Ti—Si molecular sieve and a support, based on a total amount of the catalyst, a content of the Ti—Si molecular sieve is 10-99 wt % and a content of the support is 1-90 wt %.

8. The process of claim 7, further comprising: mixing at least one organosilicon compound capable of hydrolysis and at least one water-soluble alkali with water to obtain a first mixture, mixing the first mixture the Ti—Si molecular sieve to form a second mixture, granulating and calcining the second mixture.

9. The process of claim 7, wherein the Ti—Si molecular sieve, the organosilicon compound, the water-soluble alkali and water are at a mass ratio of 100:10-2000:2-40:50-2000.

10. The process of claim 8, wherein the water-soluble alkali is a template agent for synthesizing the Ti—Si molecular sieve.

11. The process of claim 10, wherein the template agent for synthesizing the Ti—Si molecular sieve is quaternary ammonium base.

12. The process of claim 8, wherein the organosilicon compound is a compound of formula (I)

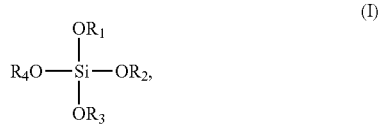

wherein each of $R_1$, $R_2$, $R_3$ and $R_4$ is $C_1$-$C_4$ alkyl.

13. The process of claim 1, wherein the Ti—Si molecular sieve is a MFI-type Ti—Si molecular sieve.

14. The process of claim 13, wherein a grain of the Ti—Si molecular sieve is a hollow structure having a cavity with a radial length of 5-300 nm, the Ti—Si molecular sieve has a benzene adsorption capacity of at least 70 mg/q, measured at 25° C., P/P0=0.10, and an adsorption time=1 hour, and there is a hysteresis loop between the adsorption isotherm and the desorption isotherm of the low temperature nitrogen adsorption of the Ti—Si molecular sieve.

15. The process of claim 1, wherein, in step (2), a molar ratio of the dimethyl sulfide feed to the oxidant is 1:0.1-2.

16. The process of claim 1, wherein the oxidant is a peroxide.

17. The process of claim 16, wherein the oxidant is hydrogen peroxide.

18. The process of claim 1, wherein, in step (2), the dimethyl sulfide feed and the solvent are at a mass ratio of 1:0.5-50.

19. The process of claim 1, wherein, in step (2), the contacting of the dimethyl sulfide feed with the at least one oxidant and the catalyst is carried out at 20-200° C. under a gauge pressure of 0.1-3 MPa.

20. The process of claim 1, wherein, in step (1), contacting hydrogen sulfide with methanol to produce the mixture containing dimethyl sulfide is conducted in the presence of γ-Al2O3.

21. The process of claim 20, wherein a weight ratio of hydrogen sulfide to γ-Al2O3 is 1:0.1-100.

22. The process of claim 1, wherein a molar ratio of hydrogen sulfide to methanol is 100-0.5:1.

23. The process of claim 1, wherein, in step (1), contacting hydrogen sulfide with methanol to produce the mixture containing dimethyl sulfide is conducted at 200-400° C.

24. The process of claim 1, wherein, in step (2), the dimethyl sulfide feed and the solvent are at a mass ratio of 1:1-20.

* * * * *